(12) United States Patent
Mach

(10) Patent No.: US 6,565,592 B2
(45) Date of Patent: May 20, 2003

(54) VEIN COMPRESSING DEVICE

(76) Inventor: Jakub Mach, Von Müllerstrasse 34, D-93437 Furth Im Wald (DE)

( * ) Notice: Subject to any disclaimer, the term of this patent is extended or adjusted under 35 U.S.C. 154(b) by 85 days.

(21) Appl. No.: 09/783,823

(22) Filed: Feb. 14, 2001

(65) Prior Publication Data

US 2001/0020176 A1 Sep. 6, 2001

(30) Foreign Application Priority Data

Feb. 17, 2000 (DE) .......................... 100 07 231

(51) Int. Cl.⁷ ................................. A61B 5/00
(52) U.S. Cl. ................. 606/202; 606/201; 600/490
(58) Field of Search ................. 606/201, 203, 606/204, 202; 604/66, 67; 600/499, 490

(56) References Cited

U.S. PATENT DOCUMENTS 5,569,304 A  * 10/1996  Ulrich ................. 606/201
5,584,853 A    12/1996  McEwen
5,911,735 A     6/1999  McEwen et al.

* cited by examiner

*Primary Examiner*—Danny Worrell
(74) *Attorney, Agent, or Firm*—Mayer, Brown, Rowe & Maw

(57) ABSTRACT

The invention relates to a vein compressing device comprising a pressure hose cuff and a pressure source as well as a pressure adjusting auxiliary means for detecting and/or adjusting the internal pressure of the cuff to a predetermined value. This pressure value causes a compressive force to act via the pressure hose cuff on the upper arm of a patient to be treated, the compressive force being large enough to cause a squeezing off of a vein while the flow area of an artery is maintained at least partly.

7 Claims, 1 Drawing Sheet

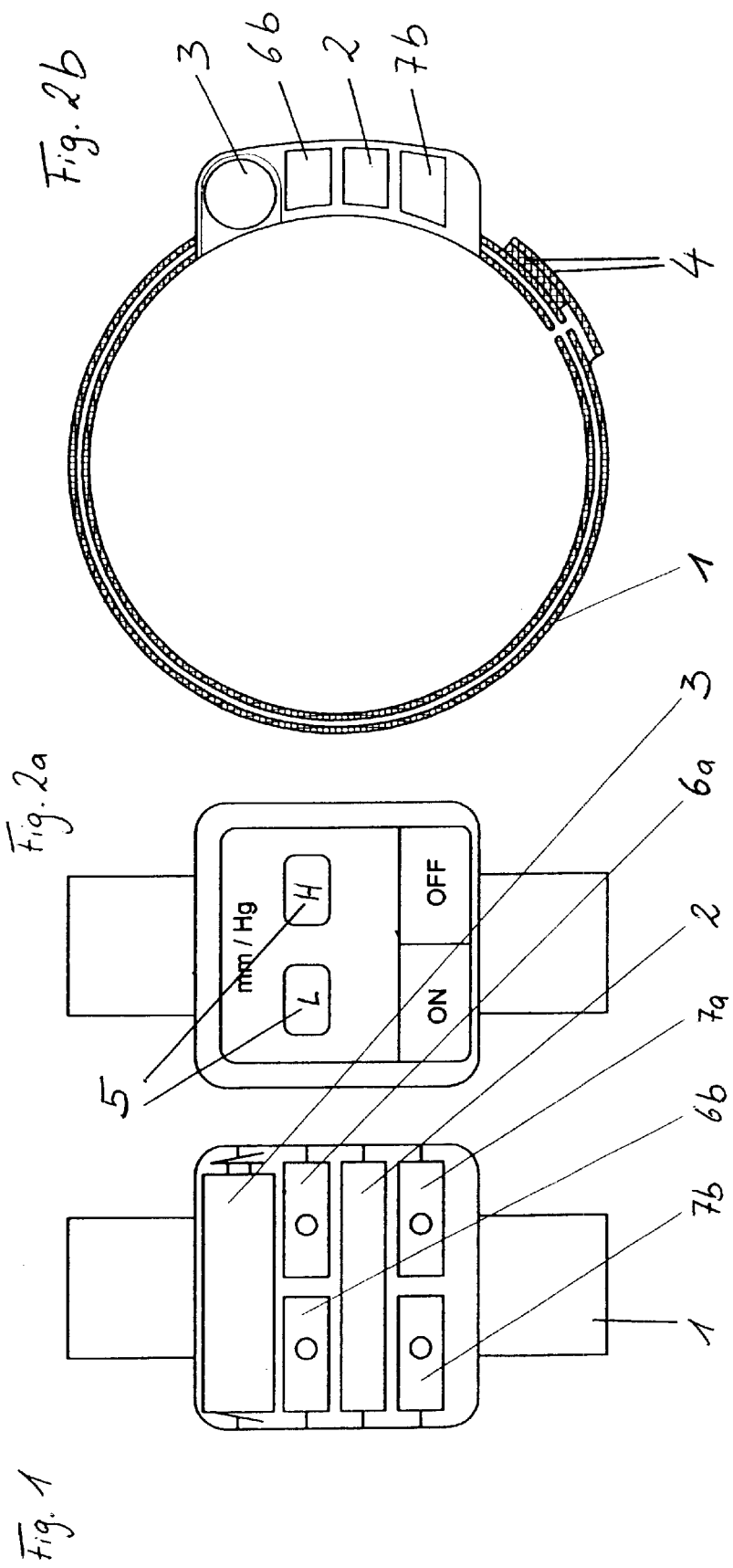

VEIN COMPRESSING DEVICE

BACKGROUND OF THE INVENTION

The present invention relates to a vein compressing/blocking device and, particularly, to a vein compressing device for application to the upper arm of a patient during blood drawing processes.

Among other things, the drawing of blood belongs to the routine work of doctors in hospitals and practices. In order to compress the veins of the upper arm of a patient for this, a venous compression tube is used. This is a flexible belt having a small clasp. This known compression tube is wound around the upper arm of a patient and tightened, which causes the veins to be squeezed off and the blood contained therein to be compressed. This, in turn, causes a bulging (swelling) of the veins, which allows the doctor to insert a cannula for drawing blood in a more precise way and, thus, to draw the blood.

However, this method is disadvantageous insofar as an attending doctor does not have any control over the amount of pressure at which the compression tube acts on the upper arm in dependence on the tensile force in the compression tube. This disadvantage is further increased by the conventional compression tubes being made of flexible material, which expands when certain tensile forces act thereon and, thus, gives the doctor an extremely "spongy" feeling of force.

Due to these insecurities of control, it often happens that not only the veins but also the lower-lying arteries of the patient to be treated are squeezed off, so that, in this case, an effect of an overfilling of the veins, which makes the veins visible, is no longer possible.

In view of this prior art, it is the object of the invention to create a vein compressing device, for example, used for drawing blood, which can be operated more exactly in order to guarantee the effect of the overfilling of the veins.

SUMMARY OF THE INVENTION

The aforementioned problems are solved by a vein compressing device comprising a pressure hose cuff having a pressure source connected thereto and a pressure adjusting auxiliary means, by means of which the inner pressure in the cuff can be detected and/or adjusted to a predetermined value. This value corresponds to a pressure causing a squeezing off of a vein, but simultaneously maintaining the flow cross-section of an artery at least partly. In this way, a blood flow in the artery can be maintained, so that the squeezed-off vein is gradually inflated by the blood compressed therein and, as a result, becomes better visible to the doctor. The predetermined pressure value has either been determined in advance by tests for different patients (age, physical constitution, different muscular systems, etc.) and stored in a table, or is calculated anew when the blood pressure is read.

Different appliances are suited for the formation of the pressure adjusting auxiliary means.

According to claim 2, a manually or electronically adjustable pressure relief valve is provided for this purpose, the pressure relief valve being disposed on the pressure hose cuff or on the pressure source. This embodiment has the advantage that no substantial technical measures have to be taken to exclude that a predetermined value is exceeded.

As an alternative, claim 1 provides that the pressure adjusting auxiliary means is formed with a pressure sensor which is connected to a microcomputer on which the predetermined value is adjusted. This embodiment facilitates the handling of the device and ensures a more exact adjustment of the inner pressure of the cuff by the feedback control process between the pressure sensor, the microcomputer, and the pressure source.

According to claim 6, a simple design of the pressure adjusting auxiliary means provides the arrangement of a simple pressure display signaling visually or acoustically that the predetermined value is reached.

Further advantageous developments of the invention are set out in the remaining claims.

BRIEF DESCRIPTION OF THE DRAWINGS

In the following, the invention will be described in greater detail by means of a preferred embodiment with reference to the accompanying drawing.

FIG. 1 shows the principle sketch of a vein compressing device according to a preferred embodiment of the invention.

FIGS. 2a and 2b show the construction of the vein compressing device comprising a microprocessor and a pressure source integrated to form a unit on the pressure cuff.

It should be understood that the Figures are not to scale. While some details of a vein compressing device and other plan and section views of the preferred embodiment depicting the invention have been omitted, such details are not considered necessary to a full and complete understanding of the invention disclosed and claimed herein. It should also be understood that the present invention is not limited to the preferred embodiment illustrated.

DETAILED DESCRIPTION OF THE PREFERRED EMBODIMENT

According to FIG. 1, the vein compressing device comprises a pressure hose cuff 1 as well as a pressure source 2 which is in fluid-communication with the pressure hose cuff 1 via a connecting passage (not shown). In the present case, the pressure source 2 is formed as a pneumatic pressure pump which is driven by a preferably battery-fed electric motor 3. As an alternative, a different power source, or a manually operated pressure pump can be provided, such as e.g., a bellows.

The pressure hose cuff 1 includes an elastic hose material which can be wound around the upper arm of a patient and can be fixed to form a closed circle. To this end, the pressure hose cuff 1. according to FIG. 2b has, at its opposite ends, velcro fastenings 4 which cooperate when the cuff 1 is put together in circular way to form a fixed connection.

Furthermore, there is provided a pressure adjusting auxiliary means including a pressure setting unit 6 and a control unit which are preferably integrated with the pressure source 2 to form a constructional unit.

The pressure setting unit 6 comprises a microcomputer (not shown in any greater detail) as well as an input component 5, for example a number of push-buttons, a dial disk, a turning knob, or any combination thereof, which is connected to the microcomputer. Furthermore, the microcomputer is connected to the control unit in the form of at least one, and in the present case two electromagnetic pressure relief valves 6a,6b as well as to the pressure source 2. Optionally, there may be provided a pressure display (not shown) which allows a visual supervision of the pressure increase or decrease within the cuff 1. As an alternative to the above-mentioned electromagnetic pressure relief valves 6a, 6b, it is possible to arrange a pressure sensor (not shown) inside the pressure source 2 or the cuff 1, said pressure sensor being electrically connected to the microcomputer. Via this pressure sensor, the microcomputer receives information on the pressure presently prevailing, so that a comparison of actual and desired pressures can be made.

Depending on the embodiment, a table of predetermined values is stored in the microcomputer, the table listing at least two different high pressure values.

It has turned out that the systolic pressure, i.e., the blood pressure within the artery, of rather young people lies at a value of about 100 to 120 mm Hg, and the diastolic pressure, i.e., the pressure inside the vein, lies at a value of about 60 to 70 mm Hg. In the case of people of a more advanced age, the systolic pressure increases to more than 120 mm Hg whereas the diastolic pressure moves to about approximately 90 mm Hg. Thus, in each case, there results a pressure range of about 30 to 40 mm Hg, but on a different level.

In a conventional method for measuring the blood pressure, there is generally also a pressure cuff put around the upper arm of a patient and then pressure is applied thereto until the flow in the vein as well as in the artery is blocked. Subsequently, the pressure inside the cuff is slowly relieved until a new blood flow is produced in the artery. The pressure measured hereby corresponds to the systolic pressure. When the pressure relief of the cuff continues, the blood flow starts anew in the vein, too, at a certain point in time, with the now prevailing pressure constituting the diastolic pressure. In this way, for every patient one can individually determine the above-mentioned pressure range. In this connection it has turned out that this pressure range differs substantially equally in young and old people, i.e., determined by age, so that it is sufficient to store at least two pressure values with respect to the used pressure hose cuff for old and young patients in the microcomputer. When doing this, the mentioned pressure range is large enough to compensate for individual deviations, for example if someone is ill or if the physical constitutions differ. In other words, at least two predetermined values are stored in dependence on the design of the pressure hose cuff, which correspond to two pressures which exert a compressive force of between 60 and 120 mm Hg, and preferably 80 and 100 mm Hg on the vein and on the artery, respectively.

It is, of course, also possible to equip the microcomputer with a blood pressure measuring function, by which means the systolic and the diastolic pressures for each patient to be treated can be measured individually and, at the same time, those two pressures which prevail inside the pressure hose cuff 1 at the respective points in time may be read. Subsequently, there is calculated a mean value between the two inner pressures of the cuff, which alternatively constitutes the predetermined value.

As a further simplification, one may omit the microcomputer altogether and, in the case of the arrangement of two pressure-relief valves, one may adjust these to the two different pressure values. The input component then has to be designed such that it directly acts on the two valves and inserts these in the pressure circuit alternatively.

Regarding the function of the vein compressing device, in the case of the table of values stored in advance, the pressure hose cuff 1 is applied to the upper arm of a patient and subsequently the suitable pressure value is selected via the pressure setting unit 6. Subsequently, the pressure pump 3 is started by the pressure setting unit or an external on/off switch 7 whereupon it raises the internal pressure inside the pressure hose cuff 1. The change in pressure is registered by the pressure sensor or by the one or the two pressure relief valves 6a,6b. When the adjusted pressure value which serves as a pressure threshold value is reached, the pressure sensor or a pressure relief valve opens and issues a signal to the microcomputer, whereupon the latter stops the pressure pump 3. In the case of the use of a pressure relief valve, the latter simultaneously prevents in any case that the predetermined pressure value is exceeded and, thus, balances any lack of control in precision, as well as delays in the control time which may occur when the pump 3 is turned off.

In case the microcomputer is additionally equipped with a blood pressure measuring function, the pressure hose cuff 1 is applied to the upper arm of the patient and, then, the pump 3 is driven in a first blood pressure measuring process until the vein as well as the artery are squeezed off. Subsequently, the blood pressure is measured individually for each patient according to the above described method.

After the internal pressures in the pressure hose cuff 1 have been detected by the pressure sensor at the time of the systolic and diastolic pressures, the microcomputer determines a mean pressure value from the detected internal pressures and drives the pressure pump 3 until this mean pressure value, which is now the predetermined pressure value, is again detected by the pressure sensor and a pertinent signal has arrived at the microcomputer.

In this case, the compressive force applied to the upper arm of the patient to be treated is exactly large enough for the vein to be completely squeezed off whereas the flow area of the artery is being maintained at least partly. Consequently, the blood flowing through the artery is exclusively compressed in the vein and causes a swelling of the vein, which makes the latter visible to the attending doctor.

Although reference has been made, for the purpose of explanation, to a preferred embodiment of a vein compressing device and methods of causing compressive force to act on the upper arm of a patient, it should be understood that any of a variety of components and suitable materials of construction and dimensions may be used to satisfy the particular needs and requirements of the end user. It will be apparent to those skilled in the art that modifications and variations can be made in the design and construction of the vein compressing device without departing from the scope or spirit of the invention. Other embodiments of the invention will be apparent to those skilled in the art from consideration of the specification and practice of the invention disclosed herein.

For example, the pressure adjusting auxiliary means may comprise, instead of the above-described pressure-relief valve(s) or the pressure sensor, a simple pressure display via which the attending doctor can read the internal cuff pressure to be used. It is also possible to combine the pressure-relief valve(s) or a pressure sensor with such a pressure display. This combination recommends itself particularly if the vein compressing device simultaneously has a blood pressure measuring function.

What is claimed is:

1. A vein compressing device comprising:

a pressure source;

a pressure hose cuff connected to said pressure source; and a pressure adjusting auxiliary means comprising a pressure setting unit for determining a value for an internal pressure in said pressure hose cuff, and a control means for adjusting the internal pressure in said pressure hose cuff to the predetermined value;

wherein said pressure setting unit further comprises:

a digital memory in which pressure values for the internal pressure in said pressure hose cuff, depending on an age and/or physical constitution of a patient, are stored;

an input component for manually imputting the age and/or the physical constitution of the patient; and a microcomputer for reading, from the memory, a suitable pressure value in dependence on the input age and/or the physical constitution of the patient, at which a squeezing off of a vein is effected while the flow area of an artery is maintained at least partly, and which controls said control means such that the internal pressure in said pressure hose cuff is kept at the pressure value read from the memory.

2. A vein compressing device according to claim 1, wherein said control means further comprises an electronically adjustable pressure-relief valve arrangement.

3. A vein compressing device according to claim 1, wherein said control means further comprises a pressure sensor connected to the computer which controls said pressure source in accordance with signals from the pressure sensor.

4. A vein compressing device according to claim 1, wherein the memory receives at least two different predetermined pressure values, the one pressure value being provided for young patients, and the other pressure value for old patients.

5. A vein compressing device comprising:

a pressure source;

a pressure hose cuff connected to said pressure source; and a pressure adjusting auxiliary means comprising a pressure setting unit for determining a value for an internal pressure in said pressure hose cuff, and a control means for adjusting the internal pressure in said pressure hose cuff to the predetermined value;

wherein said pressure setting unit further comprises:

a measuring means for determining the systolic and diastolic blood pressures of a patient; and a microcomputer including a calculating means for calculating an intermediate pressure value between the measured systolic and diastolic blood pressures, wherein said calculating means transmits the calculated intermediate pressure value to said microcomputer which adjusts, through said control means connected thereto, the internal pressure in said pressure hose cuff on the basis of the calculated intermediate pressure value to such a value that a squeezing off of a vein is effected while the flow area of an artery is maintained at least partly.

6. A vein compressing device according to claim 5, wherein said control means further comprises an electronically adjustable pressure-relief valve arrangement.

7. A vein compressing device according to claim 6, wherein said control means has a pressure sensor and controls said pressure source in response to signals from the pressure sensor.

* * * * *